(12) United States Patent
Alving et al.

(10) Patent No.: US 7,103,143 B2
(45) Date of Patent: Sep. 5, 2006

(54) X-RAY EXAMINATION APPARATUS WITH EXPOSURE CONTROL

(75) Inventors: Peter Lex Alving, Eindhoven (NL); Albert Louw Faber, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 11/127,368

(22) Filed: May 12, 2005

(65) Prior Publication Data

US 2005/0207535 A1    Sep. 22, 2005

Related U.S. Application Data

(62) Division of application No. 10/395,785, filed on Mar. 24, 2003, now Pat. No. 6,895,078.

(30) Foreign Application Priority Data

Nov. 23, 1999 (EP) ................................. 99203923

(51) Int. Cl.
  *G01B 15/02* (2006.01)
  *H05G 1/44* (2006.01)
(52) U.S. Cl. .................... 378/98.7; 378/98.8; 378/108
(58) Field of Classification Search ............... 378/98.7, 378/98.8, 108; 250/370.09
  See application file for complete search history.

(56) References Cited

U.S. PATENT DOCUMENTS

| | | | | |
|---|---|---|---|---|
| 5,029,338 A | * | 7/1991 | Aichinger et al. | ......... 378/98.7 |
| 5,485,501 A | * | 1/1996 | Aichinger | ................... 378/98.7 |
| 5,574,764 A | * | 11/1996 | Granfors et al. | ............ 378/98.7 |
| 5,710,801 A | * | 1/1998 | Dillen et al. | ................ 378/98.7 |
| 5,742,059 A | * | 4/1998 | Hassler | ................... 250/370.09 |
| 5,778,044 A | * | 7/1998 | Bruijns | ....................... 378/98.7 |
| 5,896,173 A | | 4/1999 | Hassler | |
| 5,905,772 A | | 5/1999 | Ratten et al. | |
| 6,226,351 B1 | | 5/2001 | Snoeren et al. | |
| 6,255,638 B1 | | 7/2001 | Eraluoto et al. | |
| 6,265,736 B1 | | 7/2001 | Dillen et al. | |
| 6,460,003 B1 | * | 10/2002 | Kump et al. | ................... 702/85 |

FOREIGN PATENT DOCUMENTS

DE    43 30 787 A1    3/1995

* cited by examiner

*Primary Examiner*—Edward J. Glick
*Assistant Examiner*—Irakli Kiknadze

(57) ABSTRACT

An X-ray examination apparatus includes an X-ray source, an X-ray detector and an exposure control system. The exposure control system is arranged to control the X-ray source so as to perform a test exposure at a low X-ray dose and to perform an X-ray exposure at a higher X-ray dose. The X-ray detector applies a control signal resulting from the test exposure to the exposure control system and the X-ray source is adjusted on the basis of this control signal. The X-ray exposure produces an X-ray image and the X-ray detector supplies an image signal representing this X-ray image. The exposure control system is arranged to adjust the X-ray detector to a low spatial resolution during the test exposure and to a high spatial resolution during the X-ray exposure. The X-ray detector preferably includes a sensor matrix having sensor elements arranged in columns and rows. The spatial resolution is adjusted by deriving the control signal and the image signal from large and small groups of sensor elements, respectively.

1 Claim, 2 Drawing Sheets

X-RAY EXAMINATION APPARATUS WITH EXPOSURE CONTROL

CROSS REFERENCE TO RELATED APPLICATION

This is a divisional of prior application Ser. No. 10/395,785 filed Mar. 24, 2003, and issued on May 17, 2005, as U.S. Pat. No. 6,895,078 B2.

PRIORITY

Applicants claim priority to copending U.S. patent application, Ser. No. 09/718,250 filed Nov. 22, 2000.

BACKGROUND OF THE INVENTION

1. Field of the Invention

The invention relates to an X-ray examination apparatus which includes an X-ray source, an X-ray detector, and an exposure control system for controlling the X-ray source and the X-ray detector, which exposure control system is arranged to control the X-ray source so as to carry out a test exposure with a low X-ray dose while producing a control signal by the X-ray detector, and to control the X-ray source on the basis of the control signal in order to carry out an X-ray exposure with a high X-ray dose and to acquire an X-ray image by the X-ray detector during this exposure.

2. Description of the Related Art

An X-ray examination apparatus known in the art is German Offenlegungsschrift DE 43 30 787.

An object to be examined during a radiological examination, for example a patient to be examined, is exposed to an X-ray dose in order to form one or more X-ray images of the object. The X-ray dose required for individual patients to be examined is customarily adjusted individually. The X-ray dose is adjusted by the exposure control system.

The known X-ray examination apparatus carries out the test exposure first with a comparatively low dose, thus forming a test image. During the formation of this test image, the patient to be examined is briefly exposed to X-rays with a predetermined intensity and energy. Because X-rays are applied only during a short period of time during the formation of the test image, the X-ray dose for forming the test image remains comparatively small. The test image is read out from the X-ray detector and digitized in digital grey scale values with, for example, a bit depth of 10 bits. The exposure control system of the known X-ray examination apparatus derives the X-ray dose which is required to form the X-ray image during the X-ray exposure from the distribution of the digital grey scale values. The X-ray dose required for the formation of the X-ray image is large in comparison with the X-ray dose required to form the test image. In the known X-ray examination apparatus, the larger X-ray dose is obtained by using a longer exposure time with the same intensity and energy of the X-rays as used during the test exposure. The known X-ray detector is provided with a sensor matrix having a large number of sensor elements.

It is a drawback of the known X-ray examination apparatus that the reading out of the X-ray detector after the test exposure requires the same amount of time as the reading out after the X-ray exposure whereby the X-ray image is formed. Consequently, the adjustment of the X-ray source for the X-ray exposure requires a comparatively long period of time.

SUMMARY OF THE INVENTION

It is an object of the invention to provide an X-ray examination apparatus enabling faster adjustment of the X-ray source.

This object is achieved by an X-ray examination apparatus according to the invention which is characterized in that the exposure control system is arranged to adjust the X-ray detector to a coarse spatial resolution during the execution of the test exposure, and to adjust the X-ray detector to a fine spatial resolution during the execution of the X-ray exposure.

As the X-ray detector is adjusted to a coarser resolution during the test exposure, fewer signal values need be read out from the X-ray detector. Consequently, the time required to read out the X-ray detector is shorter. Moreover, only a smaller number of signal values, for example brightness values, need be processed in order to derive the control signal therefrom; consequently, less time will also be required to form the control signal. Because the X-ray examination apparatus according to the invention requires only a short period of time for the adjustment of the X-ray examination apparatus on the basis of the test exposure, the X-ray image will become available sooner. More specifically, only a short period of time elapses between the test exposure and the X-ray exposure. Consequently, changes are less likely to occur between the test exposure and the X-ray exposure, for example due to motion in or of the object to be examined. The X-ray examination apparatus according to the invention is thus capable of quickly forming an X-ray image while ensuring that the X-ray image has a high diagnostic quality. This means that small details of low contrast are clearly reproduced nevertheless in the X-ray image. The adjustment of the X-ray examination apparatus concerns notably the adjustment of the energy and the intensity of the X-rays emitted by the X-ray source.

These and other aspects of the invention will be described in detail with reference to the following embodiments, limited only the scope of the claims appended hereto.

Preferably, the invention is used in an X-ray examination apparatus provided with an X-ray detector having a sensor matrix with a large number of sensor elements. The individual sensor elements convert incident X-rays into electric charges. The sensor matrix also includes read-out lines via which the electric charges formed in the sensor elements can be read out or detected. During the test exposure, electric charges are formed in the sensor elements. The separate signal levels of the control signal are composed of the electric charges in a comparatively small number of or in comparatively large groups of sensor elements. Such a large group contains a large number of sensor elements, i.e. more than one sensor element in any case. During the execution of the X-ray exposure, electric charges are formed again in the sensor elements. Any residual charges due to the test exposure are removed from the sensor elements. Such removal of electric charges is also called "electric reset" and is performed, for example by simultaneously reading out and draining the electric charges via all read-out lines. It is to be noted that the electric reset is known per se from U.S. Pat. No. 5,905,772 in which it is applied to counteract ghost images caused by electric charges left behind in the sensor matrix. After the X-ray exposure, the electric charges are read out again so as to form the image signal. The separate signal levels of the image signal are derived from a rather large number of or from comparatively small groups of sensor elements. Such a small group of sensor elements contains only a small number of sensor elements; for example, such a group contains only a single sensor element. The small groups of sensor elements contain fewer, preferably far fewer, sensor elements than the large groups of sensor elements. It is to be noted, however, that the sensor elements of the large groups as well as those of the small groups preferably form part of the whole assembly of sensor elements of the sensor matrix. Sensor elements may form part of a large as well as a small group. Furthermore, the sensor elements of the large as well as those of the small groups preferably have the same construction. For example, the sensor elements are constructed as photodiodes. The sensor matrix is provided with, for example, 1000×1000 or even 4000×4000 sensor elements. For example, a small group contains only a single sensor element or two neighboring sensor elements. For example, 4×4 or 32×32 large groups of sensor elements are used for the test exposure. When electric charges are combined from large groups of sensor elements, less time will be required for the reading out of the sensor matrix. The spatial resolution of the X-ray detector is coarser as electric charges from more sensor elements are combined during reading out. The spatial resolution represents the dimensions of the smallest detail that is faithfully detected by the X-ray detector. It has been found that it is not necessary for the control signal that very small details are accurately detected. The advantage of the shorter period of time that is required for the reading out of the electric charges from the large groups outweighs the loss of spatial resolution. Moreover, the signal-to-noise ratio of the control signal is higher as larger groups of sensor elements are used, i.e. as the electric charges of more sensor elements are combined during the reading out.

For the reading out of the X-ray image formed by the X-ray exposure, however, the fine spatial resolution of the X-ray detector is of importance, to ensure that small details in the X-ray image are taken up exactly in the signal levels of the image signal. This fine spatial resolution is achieved by deriving the separate signal levels of the image signal from electric charges of respective small groups which preferably contain only one or two sensor elements.

Preferably, a test image is formed by the test exposure. A measuring field is selected from such a test image. The measuring field relates to a part of the object to be examined, for example the patient, which is very relevant for the adjustment of the X-ray source. The measuring field is determined, for example, on the basis of the brightness values of the test image. The control signal is derived from the brightness values of the measuring field. Because of the use of such a measuring field it is avoided notably that the control of the X-ray source is influenced by a part of the test image which does not relate to the part of the object to be examined. Notably, X-rays which reach the X-ray detector practically without attenuation are prevented from influencing the control of the X-ray source. The adverse effects of non-attenuated X-rays on the adjustment of the X-ray source during the X-ray exposure are thus avoided. For example, a histogram analysis can be performed on the brightness values of the test image, notably in order to prevent parts of the test image which relate to substantially non-attenuated X-rays from influencing the control signal. Underexposure of the imaging of relevant parts of the anatomy in the X-ray image is thus avoided. It is to be noted, however, that from U.S. Pat. No. 5,608,775 it is known to read out only a part of the columns of sensor elements during the test exposure.

Preferably, the dose rate is derived from the control signal produced by the test exposure. The dose rate represents the energy deposited on the X-ray detector by the X-rays per unit of time. The exposure control system is preferably arranged to calculate the time integral of the dose rate during the X-ray exposure. When the X-ray exposure is performed with the same intensity and energy of the X-rays as used for the test exposure, the time integral of the dose rate can be calculated simply by multiplying the dose rate found during the test exposure by the current duration of the X-ray exposure. It is alternatively possible to use an intensity and/or energy of the X-rays during the X-ray exposure other than that used during the test exposure. In order to calculate the time integral of the dose rate it is necessary to take into account the difference in dose rate during the X-ray exposure and during the test exposure. The dependency of the dose rate on the difference between the dose rate during the test exposure and the dose rate during the X-ray exposure can be calculated or determined by calibration measurements. The dependency of the dose rate on the difference between the dose rate during the test exposure and the dose rate during the X-ray exposure can be derived, for example, by performing two successive test exposures and measuring the dose rate at a different energy and/or intensity of the X-rays. The dose rate during the X-ray exposure can be calculated or accurately estimated on the basis of these two measuring results for the dose rate, for example by interpolation or extrapolation.

The time integral of the dose rate, so the current X-ray dose, is calculated, for example at regular intervals and compared with a preset X-ray dose. As soon as the current X-ray dose reaches or exceeds the preset value, the X-ray exposure is terminated by deactivation of the X-ray source. The X-ray source is thus adjusted to deliver the required, preset X-ray dose. For example, the signal level of the control signal represents the current X-ray dose. The exposure control system compares the signal level of the control signal with a limit value. Whenever the current X-ray dose is calculated again, the signal level of the control signal is adapted and the X-ray source is deactivated as soon as the signal level exceeds the limit level. The limit level amounts to, for example 1 V. In X-ray examination apparatus it is common practice to deactivate the X-ray source when the exposure control system supplies a control signal having a signal level exceeding the limit value of 1 V. The invention can thus be simply implemented in an existing X-ray examination apparatus.

The exposure control system in another embodiment of the X-ray examination apparatus according to the invention measures the mean X-ray intensity across a test field during the X-ray exposure. Such a test field comprises a preselected group or groups of sensor elements; it has been found that columns of sensor elements which are connected to the same read-out line are suitable to act as a test field. This is because it has been found that the total charge in the sensor elements of the test field can be detected within a short period of time. Such detection is possible notably by measurement across parasitic capacitances of the sensor elements and switching elements via which the sensor elements are connected to the read-out line. The total charge can thus be detected within 100 μs; the duration of the X-ray exposure is typically from 2 to 10 ms or even 300 ms, so that the total charge can be detected twenty, one hundred or even thousands of times during the X-ray exposure. The mean intensity across the test field is thus updated during the X-ray exposure so that the current X-ray dose is known during the X-ray exposure. Individual read-out lines are connected to respective read-out amplifiers. It has been found that, due to parasitic signal transfer from the sensor elements connected (for example, per column) to the same read-out line, the output of the relevant read-out amplifier always presents a signal level which corresponds to the total charge in the sensor elements connected to the relevant read-out line. The total amount of the electric charges in the sensor elements connected to individual read-out lines can be measured at the output of the read-out amplifiers, irrespective of the control of the switching elements whereby the sensor elements are connected to the read-out lines. The sum of the electric charges in the sensor elements connected to the respective read-out line corresponds to the mean X-ray intensity incident across the sensor elements connected to respective read-out lines. Consequently, the mean X-ray intensity across the test field can be continuously measured during the X-ray exposure. When sensor elements are column-wise connected to respective read-out lines, the test field can be composed of one or more complete columns of sensor elements.

It is alternatively possible to use a plurality of read-out lines per column, each time groups of sensor elements of individual columns then being connected to individual read-out lines. Such groups of sensor elements then comprise each time parts of columns. It is then possible to compose the test field from a plurality of such groups of sensor elements. The shape and the size of the test fields can thus be selected in dependence on the architecture of the connection of the sensor elements to the read-out lines. Preferably, a reasonable correspondence exists between the test field and the measuring field; the mean X-ray intensity across the test field then yields, in conjunction with a small correction for the difference between the test field and the measuring field, the signal level for the control signal whereby the X-ray source is accurately controlled. In practice it often occurs that the test field comprises one or more complete columns of sensor elements. In that case often large differences exist between the test field and the measuring field and it is necessary to derive the control signal from the mean X-ray intensity across the test field and across the measuring field, while taking into account the difference between the test field and the measuring field. A suitable procedure for taking into account the difference between the measuring field and the test field is the determination of the ratio of the mean X-ray intensity across the measuring field to the mean X-ray intensity across the test field during the test exposure. This ratio is represented by a correction factor which amounts to the ratio of the mean X-ray intensity across the measuring field during the test exposure to the mean X-ray intensity across a test field during the test exposure. This ratio can be readily calculated on the basis of the brightnesses in the parts of the test image which correspond to the test field and the measuring field, respectively. The mean X-ray intensity across the measuring field can then also be derived during the X-ray exposure by multiplying the measured mean current X-ray intensity across the test field by the correction factor. Subsequently, time integration is applied to the current mean X-ray intensity thus calculated in order to calculate the current X-ray dose relating to the part of the patient to be examined.

BRIEF DESCRIPTION OF THE DRAWINGS

These and other aspects of the invention are apparent from and will be elucidated, by way of non-limitative example, with reference to the embodiments described hereinafter and the accompanying drawing; therein.

DETAILED DESCRIPTION OF THE PRESENTLY PREFERRED EMBODIMENTS

Figure 1:
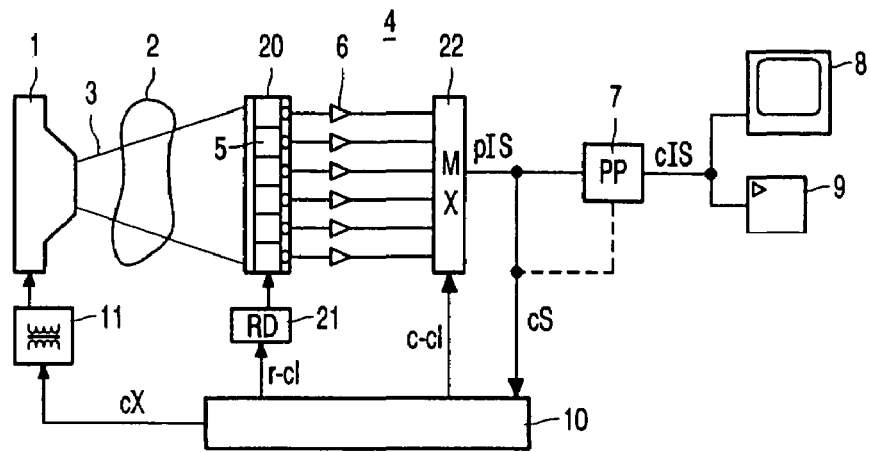
FIG. 1 shows diagrammatically an X-ray examination apparatus according to the invention.

FIG. 1 shows diagrammatically an X-ray examination apparatus according to the invention. The X-ray source 1 emits an X-ray beam 3 which irradiates an object 2 to be examined, for example a patient to be radiologically examined. The X-ray image is formed on the X-ray detector as a result of local differences in the X-ray absorption within the patient 2. The X-ray detector in the present embodiment includes an X-ray sensitive solid state sensor matrix 20 with a large number of sensor elements 5 in which electric charge carriers are released by incident X-rays. The electric charges in the sensor elements are detected (read out) via read-out amplifiers 6 so as to be applied to a multiplexer (MX) 22. For example, the read-out amplifiers form column signals whose signal levels represent the electric charges in sensor elements in respective columns of the sensor matrix. The multiplexer combines the signal levels of the column signals so as to form a primary image signal (pIS) having signal levels representing the brightness values of the X-ray image. The primary image signal is corrected for known error sources by a post-processing unit (PP) 7. These corrections concern, for example faults introduced by defective sensor elements, by sensor elements having a deviating sensitivity, faults in the read-out lines or addressing lines of the sensor matrix and, for example, undesirable crosstalk and undesirable correlations occurring upon simultaneous reading out of neighboring rows and columns of sensor elements 5. The post-processing unit delivers a corrected image signal (cIS), for example an electronic video signal, to a monitor 8 on which the information of the X-ray image is reproduced. The corrected image signal may also be applied to a buffer unit 9 in which the signal levels of the corrected image signal are stored. Using the signal levels stored in the buffer unit 9, a hard copy of the X-ray image can be formed at a later stage or further image processing operations can be performed thereon.

The X-ray examination apparatus also includes an exposure control system 10. The exposure control system is arranged to control the X-ray detector so as to produce a control signal (cS) with a coarse spatial resolution and to adjust the X-ray detector to a fine spatial resolution in order to produce the primary image signal. The exposure control system applies control signals (r-c1, c-c1) to a row driver (RD) 21 and the multiplexer 22 in order to adjust the spatial resolution during the reading out of the sensor matrix. On the basis of the control signal (cS) the exposure control system derives an X-ray control signal (cX) which is applied to a high-voltage generator 11 of the X-ray source 1. It is alternatively possible to use the post-processing unit 7 to derive the control signal (cS). In that case the multiplexer forms a mux signal in which signal levels of a plurality of column signals are summed. Subsequently, the post-processing unit 7 is used to sum signal levels of the mux signal from a plurality of rows of sensor elements in the sensor matrix, thus forming the control signal (cS). Furthermore, the post-processing unit 7 is connected to the exposure control system as indicated by a dashed line in FIG. 1.

The X-ray control signal (cX) deactivates the high-voltage generator 11 when the desired X-ray dose is reached. The X-ray control signal also controls the intensity and the energy of the X-rays. The X-ray control signal is used notably to control the high-voltage (kV) across the cathode and the anode of the X-ray source and the anode current (mA) of the X-ray source. The exposure control system 10 derives the X-ray control signal (cX) from the current X-ray dose (DX) and/or from the dose rate $r_{DX}$ as will be described in detail hereinafter with reference to FIG. 3.

Figure 2:
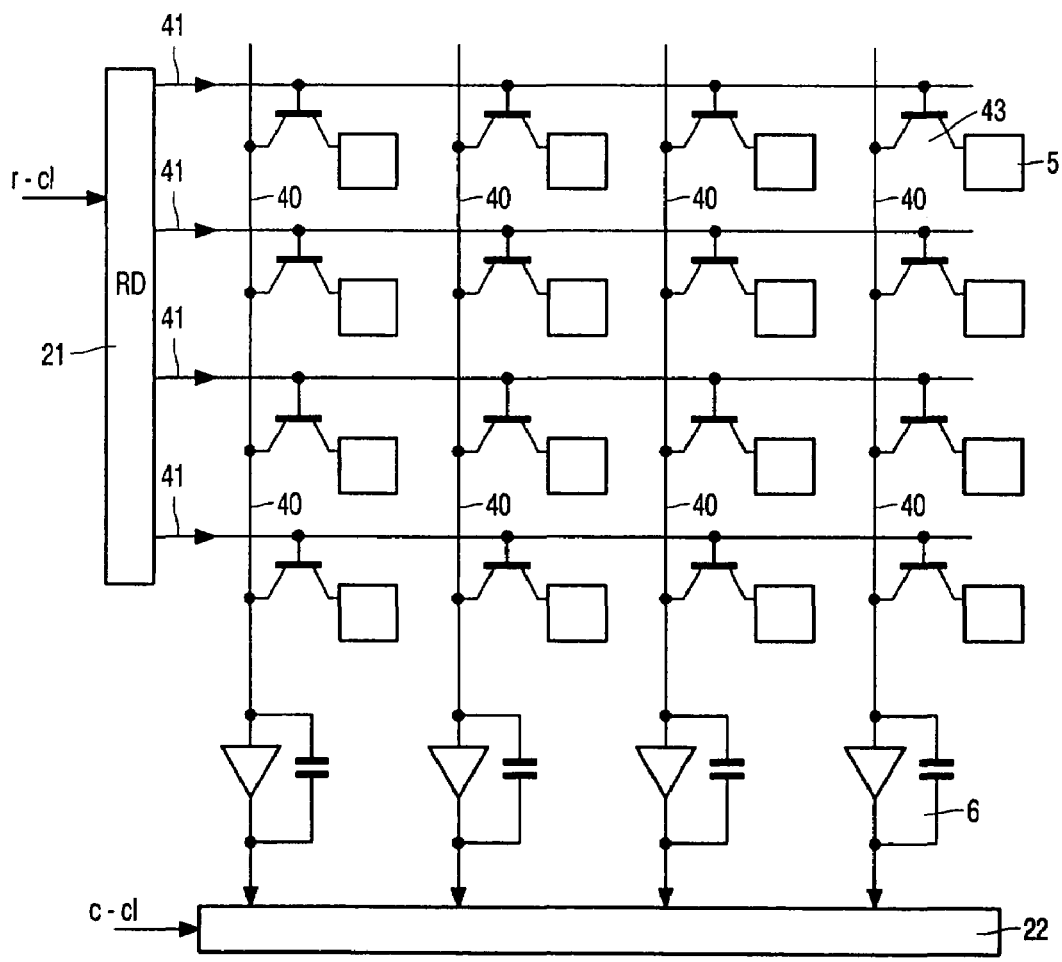
FIG. 2 shows diagrammatically a sensor matrix of the X-ray detector of the X-ray examination apparatus shown in FIG. 1.

FIG. 2 shows diagrammatically a sensor matrix of the X-ray detector of the X-ray examination apparatus shown in FIG. 1. For the sake of simplicity a sensor matrix comprising 4×4 sensor elements is shown by way of example. In practice use is made of sensor matrices comprising much larger numbers of sensor elements, for example 1000×1000, 2000×3000 or even 4000×4000 sensor elements. In the present embodiment, 2520×1920 sensor elements are preferably used. Each of the individual sensor elements has an active surface area of approximately 100 μm×100 μm or 200 μm×200 μm. The sensor elements in the matrix are connected in rows to respective addressing lines 41. The sensor elements in the matrix are connected in columns to respective read-out lines 40. Individual sensor elements are connected to the relevant addressing lines 41 by switching elements 43, for example thin-film transistors. The individual thin-film transistors are connected to the relevant read-out line 40 by way of their drain contact whereas their source contact is connected to the relevant sensor element and their gate contact is connected to the relevant addressing line. The row driver 21 applies address signals to the individual addressing lines. The address signals are applied to the gate contacts of the thin-film transistors 43 in the relevant rows in order to turn on the relevant thin-film transistors, i.e. to close the switching elements. The electric charges in the sensor elements are read out to the integrating read-out amplifiers 6 via the thin-film transistors and along the read-out lines. Thus, complete rows of the sensor matrix are read out essentially simultaneously. The integrating read-out amplifiers 6 derive the column signals in the form of electric voltages representing the respective electric charges in the sensor elements in the relevant columns. The column signals are combined in the multiplexer 22 so as to form the primary image signal or the control signal, depending on the adjustment of the X-ray detector 4 by the exposure control system 10.

Figure 3:
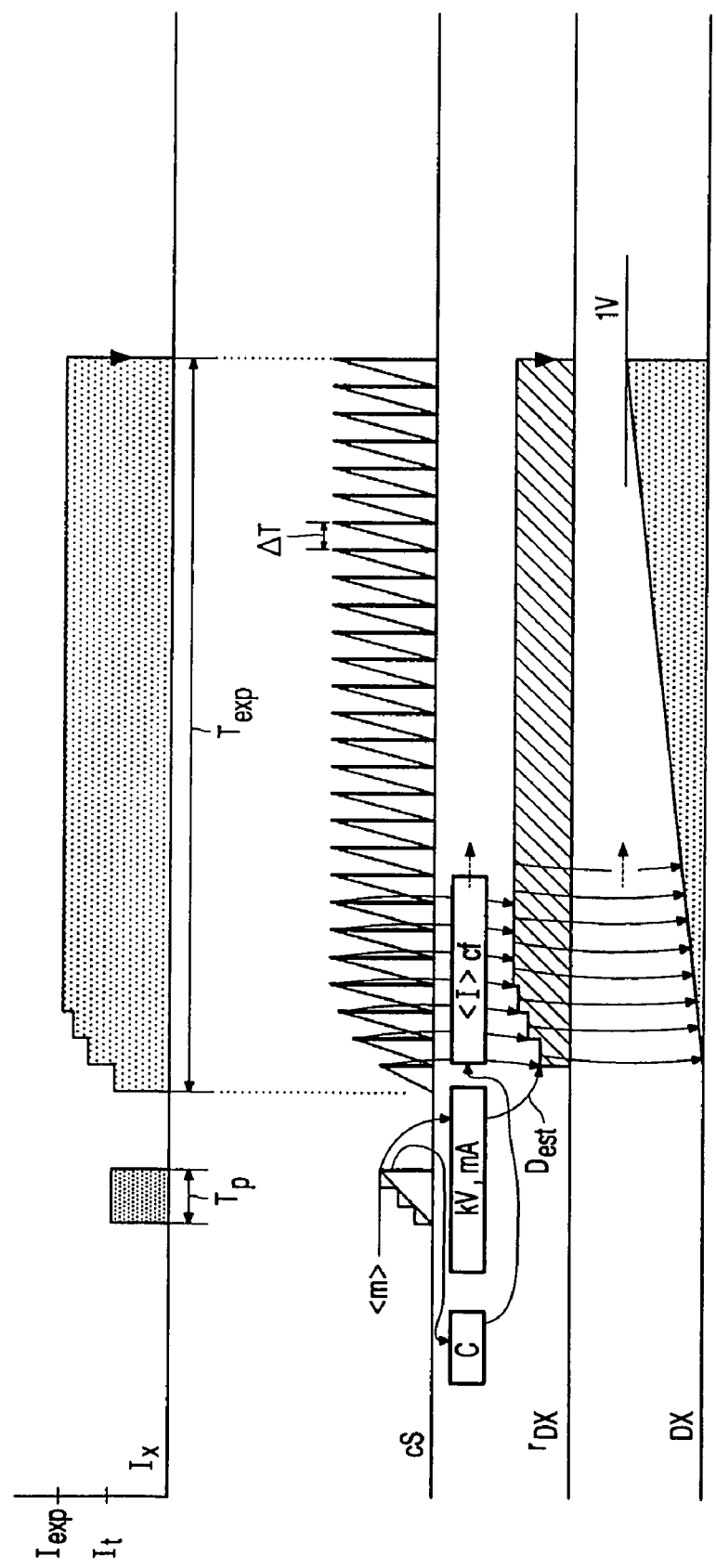
FIG. 3 is a graphic representation of the variation of various signals illustrating the operation of the exposure control system of the X-ray examination apparatus according to the invention.

FIG. 3 is a graphic representation of the variation in time of various signals illustrating the operation of the exposure control system of the X-ray examination apparatus according to the invention.

In order to carry out the test exposure, a block-shaped pulse acting as the X-ray control signal cX is applied to the high-voltage generator during a brief period of time $T_p$. As a result, the X-ray source emits an X-ray beam during the short period $T_p$. The high voltage between the cathode and the anode of the X-ray source and the anode current are pre-adjusted for the test exposure. The energy and intensity of the X-rays are thus adjusted during the test exposure. X-rays having traversed the patient during the test exposure are incident on the X-ray detector, so that the X-ray detector produces the control signal (cS). The X-ray intensity is It during the test exposure. In the example illustrated in FIG. 3, the signal level of the control signal (cS) represents the mean intensity over the pre-adjusted measuring field. One or more test images are formed by the X-ray detector during the test exposure. These test images are formed on the X-ray detector by the X-rays having traversed the patient to be examined during the test exposure. The exposure control calculates the mean intensity across the measuring field on the basis of the test image (images). During the short period $T_p$, the signal level of the control signal increases approximately step-wise, the number of steps is equal to the number of test images and the level reaches the value <m>, being the mean intensity across the measuring field. On the basis of the value <m> the exposure control system calculates an estimate of the dose rate $D_{est}$ expected to occur during the X-ray exposure. This first estimate of the dose rate is indicated in the graph of the dose rate $r_{DX}$. The exposure control system calculates the actual X-ray dose DX from the calculated dose rate $r_{DX}$. This calculation takes into account the non-linear dependency of the dose rate on the control signal. Notably non-linearities occur due to adjusting phenomena of the X-ray source which occur for a brief period of time after the activation of the X-ray source during the test exposure. Due to the short duration of the test exposure, such adjusting phenomena are significant whereas they occur to a comparatively lesser extent during the longer X-ray exposure. Moreover, a difference, if any, between the settings of the high voltage and the anode current of the X-ray source for the test exposure and for the X-ray exposure also induces a non-linear relationship between the control signal and the estimated dose rate $d_{EST}$. The non-linear relationship between the signal level of the control signal and the estimated dose rate is measured, for example, during one or more calibration exposures. This calculation of the estimated dose rate is indicated in the block "kV, mA".

The exposure control system also calculates the mean X-ray intensity across the test field from the test image. The test field concerns notably all, or practically all, columns of the sensor matrix. The exposure control system subsequently calculates the value of the correction factor $C=<I_{ij}>_{mf}/.<I_{ij}>_{cf}$, wherein $I_{ij}$ represents the brightness values in the pixel ij and $<>_{mf}, <>_{cf}$ are the mean values across the measuring field and the test field, respectively. The calculation of the correction factor is indicated by way of the block "C".

During the execution of the test exposure, the X-ray detector is read out, by way of the control signals (r-cl, c-cl) applied to the row driver 21 and the multiplexer 22, in such a manner that electric charges of, for example, 4×4, 16×16, 32×16 or 32×32 groups of several sensor elements are combined so as to form respective signal levels of the control signal (cS). Thus, the control signal represents the test image which has a comparatively coarse spatial resolution. This is because the smallest details faithfully reproduced in the test image have dimensions corresponding to the dimensions of the groups of, for example, 4×4 or 32×32 sensor elements. Moreover, during the test exposure, the exposure control system 10 measures the mean X-ray intensity across the test field of a large number of columns by measuring the signal level at the outputs of the relevant read-out amplifiers 6 by the multiplexer 22 during the test exposure. Measurements are performed on the read-out amplifiers over the parasitic capacitances in the relevant columns while the thin-film transistors are (still) open.

After the test exposure, the X-ray exposure is performed. The duration $T_{exp}$ of the X-ray exposure is considerably longer (for example, 10 ms), than the test exposure in order to ensure adequate diagnostic quality of the X-ray image. The X-ray control signal has a longer block pulse of a length (in time) $T_{exp}$ in order to activate the high-voltage generator and hence the X-ray source during the X-ray exposure. The adjustment of the X-ray source in respect of the intensity and the energy of the X-rays can be the same as during the test exposure, but this adjustment may also be changed for the X-ray exposure. At the beginning of the X-ray exposure, the X-ray intensity $I_x$ increases from the value $I_t$ to the value $I_{exp}$. Subsequently, the X-ray intensity is stabilized at the value $I_{exp}$ on the basis of the X-ray control signal.

The mean X-ray intensity across the test field is measured at regular intervals of, for example, 0.1 ms in the course of the X-ray exposure. The multiplexer 22 each time picks up the electric voltages on the output of the read-out amplifiers 6 and produces the control signal (cS) again. During this phase of the X-ray examination the signal level of the control signal (cS) initially increases; this corresponds to the increasing X-ray intensity during the readjustment of the X-ray source. On the basis of the signal level of the control signal derived from the test field and the correction factor, moreover, the current dose rate $r_{DX}$ is calculated at regular intervals and also, by integration of the current dose rate, the current X-ray dose DX. The value of the current X-ray dose is represented by an electric dose voltage in the exposure control system. The exposure control system is also arranged to compare the current X-ray dose with the preset X-ray dose. This is carried out notably by determining the instant at which the electric dose voltage reaches, for example, the limit value of 1 V. In response thereto the X-ray control signal (cX) deactivates the X-ray source and the X-ray exposure is terminated exactly when the required X-ray dose is reached. Customarily used high-voltage power supplies for the X-ray source are adjusted in such a manner that they are deactivated on the basis of an X-ray control signal of 1 V. Therefore, in order to carry out the invention the control of the high-voltage power supply need not be modified additionally.

The exposure control system includes a suitably programmed computer or (micro)processor for executing its functions and calculations.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. An X-ray examination method including an exposure control system, comprising the acts of:
    exposing an object under investigation to incident x-rays from an X-ray source;
    detecting a relative amount of attenuation passing through the object and incident upon a surface of an X-ray detector and generating a detector signal therefrom; and
    controlling the exposure of said X-ray source by an exposure control signal, the exposure control signal being derived from a plurality of brightness signal levels in a measuring field derived from respective groups of sensor elements,
    wherein the measuring field is selected by said exposure control system from a test image formed by said exposure control system,
    wherein magnitudes of said brightness signal levels are adjustable, and
    wherein a number of pixels of said test image is smaller than a number of pixels of an X-ray image acquired by said X-ray detector when said X-ray source carries out an exposure with a high X-ray dose.

* * * * *